US011031095B2

(12) United States Patent
Stuelpnagel et al.

(10) Patent No.: US 11,031,095 B2
(45) Date of Patent: Jun. 8, 2021

(54) ASSAY SYSTEMS FOR DETERMINATION OF FETAL COPY NUMBER VARIATION

(75) Inventors: John Stuelpnagel, San Jose, CA (US); Ken Song, San Jose, CA (US); Arnold Oliphant, San Jose, CA (US); Craig Struble, San Jose, CA (US)

(73) Assignee: Ariosa Diagnostics, Inc., San Jose, CA (US)

( * ) Notice: Subject to any disclaimer, the term of this patent is extended or adjusted under 35 U.S.C. 154(b) by 1084 days.

(21) Appl. No.: 13/426,157

(22) Filed: Mar. 21, 2012

(65) Prior Publication Data
US 2012/0191367 A1      Jul. 26, 2012

Related U.S. Application Data

(63) Continuation-in-part of application No. 13/338,963, filed on Dec. 28, 2011, now Pat. No. 8,700,338, which is a continuation-in-part of application No. 13/316,154, filed on Dec. 9, 2011, now abandoned, application No. 13/426,157, filed on Mar. 21, 2012, which is a continuation-in-part of application No. 13/205,570, filed on Aug. 8, 2011, now Pat. No. 9,890,421, which is a continuation-in-part of application No. 13/013,732, filed on Jan. 25, 2011, now abandoned.

(60) Provisional application No. 61/436,135, filed on Jan. 25, 2011, provisional application No. 61/371,605, filed on Aug. 6, 2010.

(51) Int. Cl.
*G01N 33/48* (2006.01)
*G01N 33/50* (2006.01)
*G16B 20/00* (2019.01)

(52) U.S. Cl.
CPC .................................. *G16B 20/00* (2019.02)

(58) Field of Classification Search
CPC ..................................................... G16B 20/00
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,136,229 A | 10/2000 | Cui et al. |
| 6,141,096 A | 10/2000 | Stern et al. |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |

(Continued)

FOREIGN PATENT DOCUMENTS

| | | |
|---|---|---|
| GB | 2299166 | 9/1996 |
| GB | 970444 | 3/1997 |

(Continued)

OTHER PUBLICATIONS

Wong et al. A comprehensive analysis of common copy-number variations in the human genome. The American Journal of Human Genetics, vol. 80, pp. 91-104. (Year: 2007).*

(Continued)

*Primary Examiner* — Russell S Negin
(74) *Attorney, Agent, or Firm* — Mintz Levin Cohn Ferris Glovsky and Popeo, P.C.

(57) ABSTRACT

The present invention provides processes for determining accurate risk probabilities for chromosome dosage abnormalities. Specifically, the invention provides non-invasive evaluation of genomic variations through chromosome-selective sequencing and non-host fraction data analysis of maternal samples.

18 Claims, 1 Drawing Sheet

(56) References Cited

U.S. PATENT DOCUMENTS

| | | |
|---|---|---|
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Lo |
| 6,949,370 B1 | 9/2005 | Barany et al. |
| 6,977,162 B2 | 12/2005 | Dhallan |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Barany et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,293,076 B2 | 10/2012 | Fan et al. |
| 8,700,338 B2 | 4/2014 | Oliphant et al. |
| 10,131,937 B2 | 11/2018 | Sparks et al. |
| 2002/0045176 A1 | 4/2002 | Lo |
| 2002/0132241 A1 | 9/2002 | Fan et al. |
| 2003/0003459 A1 | 1/2003 | Stahl |
| 2003/0044388 A1 | 3/2003 | Lo et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2003/0186239 A1* | 10/2003 | Dhallan .............. C12Q 1/6806 435/6.12 |
| 2004/0009518 A1 | 1/2004 | Lo et al. |
| 2004/0101835 A1 | 5/2004 | Willis et al. |
| 2004/0203037 A1 | 10/2004 | Lo et al. |
| 2004/0214175 A9 | 10/2004 | McKernan et al. |
| 2005/0095618 A1 | 5/2005 | Tsui et al. |
| 2005/0191656 A1 | 9/2005 | Drmanac et al. |
| 2006/0121452 A1 | 6/2006 | Dhallan |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1* | 1/2008 | Mitchell .............. C12Q 1/6883 435/6.12 |
| 2008/0070792 A1* | 3/2008 | Stoughton et al. ............... 506/9 |
| 2008/0081338 A1 | 4/2008 | Lo et al. |
| 2008/0096766 A1 | 4/2008 | Lee |
| 2008/0138809 A1 | 6/2008 | Kapur et al. |
| 2008/0206749 A1 | 8/2008 | Olson et al. |
| 2008/0243398 A1 | 10/2008 | Rabinowitz |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1* | 6/2011 | Fan ...................... C12Q 1/6851 435/6.12 |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0039724 A1 | 2/2012 | Rossi |

(56) References Cited

U.S. PATENT DOCUMENTS

| | | | |
|---|---|---|---|
| 2012/0100548 A1 | 4/2012 | Rava et al. | |
| 2012/0108460 A1 | 5/2012 | Quake et al. | |
| 2012/0165203 A1 | 6/2012 | Quake et al. | |
| 2012/0184449 A1 | 6/2012 | Hixson | |
| 2012/0191359 A1 | 7/2012 | Oliphant et al. | |
| 2012/0191367 A1 | 7/2012 | Stuelpnagel et al. | |
| 2012/0219950 A1 | 8/2012 | Oliphant et al. | |
| 2012/0225798 A1 | 9/2012 | Cantor et al. | |
| 2012/0230258 A1 | 9/2012 | Rava et al. | |
| 2012/0237928 A1 | 9/2012 | Rava et al. | |
| 2012/0264115 A1 | 10/2012 | Rava | |
| 2012/0264121 A1 | 10/2012 | Rava et al. | |
| 2012/0270739 A1 | 10/2012 | Rava et al. | |
| 2013/0029852 A1 | 1/2013 | Rava | |
| 2013/0090250 A1 | 4/2013 | Sparks et al. | |

FOREIGN PATENT DOCUMENTS

| | | | |
|---|---|---|---|
| GB | 9704444.0 | 3/1997 | |
| WO | WO87/006270 | 4/1987 | |
| WO | WO90/06995 | 6/1990 | |
| WO | WO99/47964 | 9/1999 | |
| WO | WO2003/038120 | 5/2003 | |
| WO | WO2007/100243 | 9/2007 | |
| WO | WO2007/126377 | 11/2007 | |
| WO | WO-2007147074 A2 * | 12/2007 | ........... C12Q 1/6883 |
| WO | WO2008/118998 | 10/2008 | |
| WO | WO 2009/036525 | 3/2009 | |
| WO | WO2009/102632 | 8/2009 | |
| WO | WO2011/090556 | 1/2010 | |
| WO | WO2011/090557 | 1/2010 | |
| WO | WO2011/090558 | 1/2010 | |

OTHER PUBLICATIONS

Cooper et al. Diagnosis of genetic disease using recombinant DNA. Second Edition. Human Genetics, vol. 83, pp. 307-334. (Year: 1989).*
International Search Report for PCT/US2011/046981, dated Oct. 15, 2012.
Final Office Action dated Dec. 7, 2012 on U.S. Appl. No. 13/013,732.
Final Office Action dated Oct. 12, 2012 on U.S. Appl. No. 13/013,732.
Search Report Received on May 11, 2012 for (PCT/US2012/022261).
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.
Bodurtha and Strauss, "Genomics and Prenatal Care", New Eng. J. of Medicine, 366:64-73 (2012).
Chiu, et al., "Noninvasive prenatal diagnosis of fetal chromosomal aneuploidy by massively parallel genomic sequencing of DNA in maternal plasma", PNAS USA 105:20458-63 (2008) Supporting Information.
Sparks, et al., "Noninvasive prenatal detection and selective analysis of cell-free DNA obtained from maternal blood: evaluation for trisomy 21 and trisomy 18", Am. J. Obstet. Gynecol., (2012), 206:319.e1-9.
Sparks, et al., "Selective analysis of cell-free DNA in maternal blood for evaluation of fetal trisomy", Prenatal Diagnosis, 32:1-7 (2012).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030.
Enders, et al., "Fetal morbidity and mortality after acute human parvovirus B19 infection in pregnancy: prospective evaluation of 1018 cases", Prenatal Diagnosis, 24:513-18 (2004).
Smith, et al., "Quantitative phenotyping via deep barcode sequencing", Genome Res., 19:1836-42 (2009).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Xie and Tammi, "CNV-seq, a new method to detect copy number variation using high throughput sequencing", BMC Bioinformatics, 10:80 (2008), doi 10.1186/1471-2105-10-80, p. 1-9.
Office Action Received on Apr. 15, 2013 for U.S. Appl. No. 13/356,133 (inventor A. Oliphant, filed Jan. 23, 2012), entire document.
Office Action Received on May 17, 2013 for U.S. Appl. No. 13/356,575 (inventor A. Oliphant, filed Jan. 23, 2012), entire document.
Office Action Received on Apr. 5, 2013 for U.S. Appl. No. 13/689,206 (inventor A. Oliphant, filed Nov. 39, 2012).
Final Office Action Received on Jul. 8, 2013 for U.S. Appl. No. 13/689,206 (inventor A. Oliphant, filed Nov. 39, 2012), entire document.
Office Action Received on Jul. 5, 2012 for U.S. Appl. No. 13/013,732 (inventor A. Oliphant, filed Jun. 25, 2011).
Office Action Received on Dec. 7, 2012 for U.S. Appl. No. 13/013,732 (inventor A. Oliphant, filed Jun. 25, 2011), entire document.
Office Action Received on Apr. 11, 2013 for U.S. Appl. No. 13/013,732 (inventor A. Oliphant, filed Jun. 25, 2011), entire document.
Office Action Received on May 13, 2013 for U.S. Appl. No. 13/407,978 (inventor K. Song, filed Feb. 29, 2012), entire document.
Office Action Received on Jul. 8, 2013 for U.S. Appl. No. 13/205,490 (inventor A. Sparks, filed Aug. 8, 2011), entire document.
Office Action Received on Mar. 28, 2013 for U.S. Appl. No. 13/687,169 (inventor A. Sparks, filed Nov. 28, 2012), entire document.
Office Action Received on Feb. 28, 2013 for U.S. Appl. No. 13/205,570 (inventor A. Sparks, filed Aug. 8, 2011), entire document.
Office Action Received on Mar. 14, 2013 for U.S. Appl. No. 13/687,025 (inventor A. Sparks, filed Nov. 28, 2012), entire document.
Office Action Received on May 10, 2012 for U.S. Appl. No. 13/293,419 (inventor A. Sparks, filed Nov. 10, 2011), entire document.
Office Action Received on Aug. 22, 2012 for U.S. Appl. No. 13/293,419 (inventor A. Sparks, filed Nov. 10, 2011), entire document.
Final Office Action Received on Oct. 12, 2012 for U.S. Appl. No. 13/293,419 (inventor A. Sparks, filed Nov. 10, 2011), entire document.
Advisory Action Received on Jan. 29, 2013 for U.S. Appl. No. 13/293,419 (inventor A. Sparks, filed Nov. 10, 2011), entire document.
Office Action Received on Feb. 28, 2013 for U.S. Appl. No. 13/245,133(inventor A. Oliphant, filed Sep. 26, 2011), entire document.
Office Action Received on Jun. 13, 2013 for U.S. Appl. No. 13/316,154 (inventor A. Oliphant, filed Dec. 9, 2011), entire document.
Office Action Received on Jun. 13, 2013 for U.S. Appl. No. 13/338,963 (inventor A. Oliphant, filed Dec. 28, 2011), entire document.
Office Action Received on Feb. 15, 2013 for U.S. Appl. No. 13/689,417 (inventor A. Oliphant, filed Nov. 29, 2012), entire document.
Search Report Received on Feb. 21, 2013 for (PCT/US2011/046963), entire document.
Search Report Received on Apr. 19, 2013 for (PCT/US2012/70177), entire document.
Bianchi, et al., "Large Amounts of Cell-free DNAS Are Present in Amniotic Fluid", Clin. Chem., 47(10) 1867-69 (2001).
Centre for Genomics Education, "Changes to Chromosome Structure—Translocations", The Australasian Genetics Resource Book, www.genetics com, pp. 1-5 (2007).

(56) References Cited

OTHER PUBLICATIONS

Chiu, et al., "Non-invasive prenatal diagnosis by single molecule counting technologies", Trends in Genomics, 25(7):324-31 (2009).
Hayden, et al., "Multiplex-Ready PCR: A new method for multiplexed SSR and SNP genotyping", BMC Genomics, 9:80:1-12 (2007).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2002).
Indolfi, et al., "Perinatal Transmission of Hepatitis C Virus Infection", J. Med. Virol., 81:836-43 (2009).
Mardis, et al., "The impact of next-generation sequencing technology on genetics", Trends in Genetics, 24(3):133-41 (2007).
Porreca, et al., "Multiplex amplification of large sets of human exons", Nat. Methods, 4(11):931-36 (2007).
Schouten, et al., "Relative quantification of 40 nucleic acid sequences by multiplex ligation-dependent probe amplification", Nuc. Ac. Res., 30(12):e57 (2002).
Tewhey, et al., "Microdroplet-based PCR enrichment for large-scale targeted sequencing", Nat. Biotech., 27(11):1025-31 (2009).
Zolotukhina, et al., "Analysis of Cell-free DNA in Plasma and Serum of Pregnant Women", J. of Hist. and Cytochem., 53:297-99 (2005).
Office Action Received on Oct. 31, 2013 for U.S. Appl. No. 13/356,575 filed Jan. 23, 2012, inventor Oliphant, entire document.
Office Action Received on Jun. 25, 2014 for U.S. Appl. No. 13/689,206, filed Nov. 29, 2012, inventor Oliphant, entire document.
Office Action Received on Feb. 11, 2014 for U.S. Appl. No. 13/689,206, filed Nov. 29, 2012, inventor Oliphant, entire document.
Office Action Received on Jun. 26, 2014 for U.S. Appl. No. 13/356,133, filed Jan. 23, 2012, inventor Oliphant, entire document.
Office Action Received on Oct. 18, 2013 for U.S. Appl. No. 13/356,133, filed Jan. 23, 2012, inventor Oliphant, entire document.
Office Action Received on Jul. 31, 2013 for U.S. Appl. No. 13/013,732, filed Jun. 25, 2011, inventor Oliphant, entire document.
Office Action Received on Apr. 14, 2014 for U.S. Appl. No. 13/013,732, filed Jun. 25, 2011, inventor Oliphant, entire document.
Office Action Received on Feb. 11, 2014 for U.S. Appl. No. 13/405,839, filed Feb. 27, 2012, inventor Oliphant, entire document.
Office Action Received on Oct. 25, 2013 for U.S. Appl. No. 13/407,978, filed Feb. 29, 2012, inventor Song, entire document.
Office Action Received on Jul. 30, 2014 for U.S. Appl. No. 13/407,978, filed Feb. 29, 2012, inventor Song, entire document.
Office Action Received on Jan. 31, 2014 for U.S. Appl. No. 13/605,505, filed Sep. 6, 2012, inventor Struble, entire document.
Office Action Received on Aug. 8, 2013 for U.S. Appl. No. 13/605,505, filed Sep. 6, 2012, inventor Struble, entire document.
Office Action Received on Aug. 30, 2013 for U.S. Appl. No. 13/687,169, filed Nov. 28, 2012, inventor Sparks, entire document.
Office Action Received on May 8, 2014 for U.S. Appl. No. 13/687,169, filed Nov. 28, 2012, inventor Sparks, entire document.
Office Action Received on Dec. 10, 2013 for U.S. Appl. No. 13/205,490, filed Aug. 8, 2011, inventor Sparks, entire document.
Office Action Received on Jul. 8, 2013 for U.S. Appl. No. 13/205,490, filed Aug. 8, 2011, inventor Sparks, entire document.
Office Action Received on Oct. 2, 2013 for U.S. Appl. No. 13/687,025, filed Nov. 28, 2012, inventor Sparks, entire document.
Office Action Received on Jul. 16, 2014 for U.S. Appl. No. 13/687,025, filed Nov. 28, 2011, inventor Sparks, entire document.
Office Action Received on Aug. 30, 2013 for U.S. Appl. No. 13/205,570, filed Aug. 8, 2011, inventor Sparks, entire document.
Office Action Received on May 8, 2014 for U.S. Appl. No. 13/205,570, filed Aug. 8, 2011, inventor Sparks, entire document.
Office Action Received on Jul. 14, 2014 for U.S. Appl. No. 13/293,419, filed Nov. 10, 2011, Sparks, entire document.
Office Action Received on Jun. 26, 2014 for U.S. Appl. No. 13/205,603, filed Aug. 8, 2011, inventor Sparks, entire document.
Office Action Received on Dec. 30, 2013 for U.S. Appl. No. 13/205,603, filed Aug. 8, 2011, inventor Sparks, entire document.
Office Action Received on Dec. 11, 2013 for U.S. Appl. No. 13/274,309, filed Oct. 15, 2011, inventor Struble, entire document.
Office Action Received on Aug. 30, 2013 for U.S. Appl. No. 13/245,133, filed Sep. 26, 2011, inventor Oliphant, entire document.
Office Action Received on Feb. 28, 2013 for U.S. Appl. No. 13/245,133, filed Sep. 26, 2011, inventor Oliphant, entire document.
Office Action Received on May 8, 2014 for U.S. Appl. No. 13/245,133, filed Sep. 26, 2011, inventor Oliphant, entire document.
Office Action Received on May 12, 2014 for U.S. Appl. No. 13/689,417, filed Nov. 29, 2012, inventor Oliphant, entire document.
Office Action Received on Oct. 31, 2013, filed Dec. 9, 2011, inventor Oliphant for U.S. Appl. No. 13/316,154, entire document.
Australian Patent Examination Report No. 1 dated Feb. 20, 2014 for 2011285512, entire document.
Australian Patent Examination Report No. 1 dated Mar. 4, 2014 for 2011285518, entire document.
Australian Patent Examination Report No. 1 dated Feb. 7, 2014 for 2011285477, entire document.
EPO Examination Report dated Nov. 21, 2013 for App. No. 11745880.2, entire document.
EPO Examination Report dated Nov. 21, 2013 for App. No. 11745881.1, entire document.
EPO Examination Report dated Nov. 28, 2013 for App. No. 11745883.6, entire document.
Search Report dated Sep. 12, 2013 for PCT/US 2012/026754, entire document.
Search Report dated Nov. 15, 2013 for PCT/US 2013/51310, entire document.
Search Report dated May 14, 2013 for PCT/US 2014/17092, entire document.
Search Report dated Aug. 12, 2014 for PCT/US2013/75683, entire document.
Shapiro, et al., "Determination of Circulating DNA Levels in Patients with Benign or Malignant Gastrointestinal Disease", Cancer, 51:2116-20 (1983).
Sparks, et al., "Non-invasive Prenatal Detection and Selective Analysis of Cell-free DNA Obtained from Maternal Blood: Evaluation for Trisomy 21 and Trisomy 18", Am. J. Obstet. Gynecol., (2012), doi:10.1016/j.ajog.2012.01.030, entire document.
Sullivan, et al., "Evidence for Structural Heterogeneity from Molecular Cytogenetic Analysis of Dicentric Robertsonian Translocations", Am. J. Hum. Genet., 59:167-75 (1996).
Search Report Received on May 11, 2012 for (PCT/US2012/022261), entire document.
Search Report Received on Oct. 15, 2012 for (PCT/US2011/046981), entire document.
Search Report Received on Aug. 13, 2012 for (PCT/US2011/046976).
Office Action Received on Jul. 5, 2012 for U.S. Appl. No. 13/013,732.
Abadia-Molina, et al., "Immune phenotype and cytotoxic activity of lymploycytes from human term decidua against trophoblast", J. of Reproductive Immunology, n31:109-23 (1996).
Anker, et al., "Spontaneous Release of DNA by Human Blood Lymphocytes as Shown in an in Vitro System", Cancer Research, 35:2375-82 (1975).
Anker, et al., "K-ras Mutations are found in DNA extreacted from the plasma of patients with colorectal cancer," Gastroenterology, 112:1114-20 (1997).
Anker, et al., Information carried by the DNA release by antigen-stimulated lymphocytes:, Immunology, 37:753-63 (1979).
Ashoor, et al., Fetal Fraction in Maternal Plasma Cell-Free DNA at 11-13 Weeks' Gestation: Effect of Maternal and Fetal Factors, Fetal Dian Ther DOI:10.1159/000337373 (Pub'd online May 4, 2012).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-61.

(56) References Cited

OTHER PUBLICATIONS

Belokhvostov, et al., "Changes in the Fractional Composition of the Nucleic Acids in Blood Serum upon Rediation Damage Early Stage Abnormalities Following Gamma-Irradiation of Rats", Tsitologiia (Cytology) 1986.
Bradstock, et al., "Functional and phenotypic assessment of neonatal human leucocytes expressing natural killer cell-associated antigen", Immunology and Cell Biology (71:535-42 (1993).
Campbell, et al., "Subclonal phylogenetic structions in cancer revealed by ultra-deep sequencing", PNAS, 105(35):13081-86 (2008).
Cicuttini and Boyd, "Hemopoietic and Lymphoid Progenitro Cells in Human Umbilical Cord Blood", Developmental Immunology, 4:1-11 (1994).
Datta, et al., "Sensitive Detection of Occult Breast Cancer by the Reverse-Transcriptase Polymerase Chain Reaction", J. of Clinical Oncology, 12(3): 475-82 (1994).
Dennin, "DNA of Free and Complexed Origin in Human Plasma: Concentration and Length Distribution", Klin. Wochenschr., 57:451-56 (1979).
Fisher, et al., "Genetic evidence that placental site trophoblastic tumours can originate from a hydatidiform mole or a normal conceptus", Br. J. Cancer, 65:355-358 (1992).
Fournie, et al., "Plasma DNA as Cell Death Marker in Elderly Patients", Gerontology, 39:215-221 (1993).
Geifman-Holzman, et al., "Fetal RhD genotyping in fetal cells flow sorted from maternal blood", Am. J. Obstet. Gynecol., 174(3):818-22 (1996).
Ghossein, et al.. "Detection of Circulating Tumor Cells in Patients With Localized and Metastatic Prostatic Carcinoma Clinical Implications", J. of Clin. Oncology, 13(5):1995-200 (1995).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Heid, et al., "Real Time Quantitative PCR", Genome Res., 6:986-94 (1996).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
International Human Genome Sequencing Consortium, "Initial sequencing and analysis of the human genome", Nature, 409:860-921 (2001).
Kazakov, et al., "Extracellular DNA in the Blood of Pregnant Women", Tsitologiia (Cytology), 37(3):232-37 (1995).
Kogan, et al., "An improved method for prenatal diagnosis of genetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Margulies, et al., "Genome sequencing in microfabricated high-density picolitre reactors", Nature, 437(15):376-80 and errata (2005).
Mikhaylov, et al., "Changes in the quantity and synthesis of DNA in the nuclei of large decidual cells of rats in the course of their differentiation", Tsitologiia (Cytology),41(6):677-83.
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.

Moreno and Gomella, "Circulating Prostate Cancer Cells Detected by Reverse Transcription-Polymerase Chain Reaction (RT-PCR: What do they mean?", Cancer Control Journal, 5(6).
Mulcahy, et al., "Plasma DNA K-rase Mutations in Patients with Gastrointestinal Malignancies," Annals New York Academy of Sciences, 25-28.
Nelson, et al., "Alu polymerase chain reaction: A method for rapid isolation of human-specific sequence from complex DNA sources," PNAS USA, 86:6686-90 (1989).
Paolella, et al., "The Alu family repeat promoter has a tRNA-like bipartite structure", EMBO J., 2(5):691-96.
Oei, et al., "Clusters of regulatory signals for RNA polymerase II transcription associated with Alu family repeats and CpG islands in human promoters", Genomics, 83:873-82 (2004).
Robbins, et al., *Pathologic Basis of Disease $5^{th}$ Ed.*, Chapter 23, pp. 1071-88 (1994).
Ronaghi, et al., "A Sequencing Method Based on Real_Time Pyrophosphate", Science, 281:363-65 (1998).
Saiki, et al., "Primer-directed Enzymatic Amplification of DNA with a Thermostable DNA Polymerase", Science, 239:487-91 (1987).
Schallhammer, et al., "Phenotypic comparison of natural killer cells from peripheral blood and from early pregnancy decidua", Early Pregnancy: Biology and Medicine, 3:15-22 (1997).
Schroder, et al., "Transplacental passage of blood cells", J. of Medical Genetics, 12:230-42 (1974).
Shendure, et al., "Accurate Multiplex Polony Sequencing of an Evolved Bacterial Genome", Science, 309:1728-32 (2005).
Simpson, et al., "Isolating Fetal Cells in Maternal Circulation for Prenatal Diagnosis", Prenatal Diagnosis, 14:1229-42 (1994).
Smith, et al.,"Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Sorenson, et al., "Soluble normal and mutated DNA sequences from single-copy genes in human blood", Cancer Epidemmiol. Biomarkers, 3:64-71 (1994).
Stroun, et al., "Circulating Nulceic Acids in Higher Organisms", Rev. Cytol. 51:1-48 (1977).
Stroun, et al., The Origin and Mechanism of Circulating DNA, Annals New York Academy of Sciences, 906:161-68 (2000).
Tagle, et al., "An optimized Alu-PCR primer pair for human-specific amplification of YACs and somatic cells hybrids", Human Molecular Genetics, 1(2):121-22 (1992).
Tomilin, et al., "Mechanisms of Chromosome Destabilization in Human Cells", Sov. Sci. Rev. D. Physiochem. Biol., 10:39-89 (1992).
Ulbright, "Germ cell tumors of the gonads: a selective review emphasizing problems in differential diagnosis, newly appreciated, and controversial issues," Modern Pathology, 18:S61-S79 (2005).
Vasioukhin, et al., "Point mutations in the N-ras gene in the blood plasma DNA of patients with myelodysplastic cyndrome or acute myelogenous leukaemia", British J. of Haematology, 86:774-79 (1994).
Walker, et al., "Human DNA quantitation using Alu element-based polymerase chain reaction", Analytical Biochem., 315:122-28 (2003).
Witt, et al., "An improved, non-isotopic method of screening cells from patients with abnormalities of sexual differentiation for Y chromosomal DNA content", J. Med. Genet., 30:304-07 (1993).
Stroun, et al., "Neoplastic Characteristics of the DNA Found in the Plasma of Cancer Patients", Oncology, 46:318-322 (1989).
Stroun, et al., "Isolation and Characterization of DNA from the Plasma of Cancer Patients", Eur. J. Cancer Clin. Oncol., 23(6)707-12 (1987).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Systematic microarray-based identification of placental mRNA in maternal plasma: towards non-invasive prenatal gene expression profiling", J. Med Genet, 41:461-67 (2004).
Tsui, et al., "Noninvasive prenatal diagnosis of hemophilia by microfluidics digital PCR analysis of maternal plasma DNA", Blood, 117:3684=91 (2011).

(56) References Cited

OTHER PUBLICATIONS

Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Maternal serum screening for Down's syndrome in early pregnancy", BMJ, 297:883-87 (1988).
Wald, et al., "Antenatal maternal serum screening for Down's syndrome: results of a demonstration project", BMJ, 305(6850):391-94 (1992).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Wu and Wallace, "The ligation amplification reaction (LAR)—Amplification of specific DNA sequences using sequential rounds of template-dependent ligation", Genomics, 4:560-69 (1989).
Young and Davis, "Efficient isolation of genes by using antibody probes", PNAS 80:1194-98 (1983).
Lapair, et al., "Cell-Free DNA in Amniotic Fluid: Unique Fragmentation Signatures in Euploid and Aneuploid Fetuses", Clinical Chem., 53(3):405-11 (2007).
Office Action Received on May 10, 2012 for U.S. Appl. No. 13/293,419.
Search Report Received on Jan. 20, 2012 for (PCT/US2012/21955).
Search Report Received on May 2, 2012 for PCT/US2011/046935.
Search Report Received on May 10, 2012 for (PCT/US2012/026754).
Agostini, et al., "Circulating cell-free DNA: a promising marker of pathologic tumor response in rectal cancer patients receiving pre-operative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (1003).
Arnheim, et al., "Molecular evidence for genetic exchanges among ribosomal genes on nonhomologous chromosomes in man and apes", PNAS USA, 77(12):7323-27 (1980).
Bandyopadhyay, et al, "Identification and characterization of satellite III subfamilies to the acrocentric chromosomes", Chromosome Research, 9:223-33 (2001).
Bianchi, "Prenatal diagnosis by analysis of fetal cells in maternal blood", J. of Pediatrics, 127(6):847-56 (1995).
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bombard, et al., "Fetal RHD genotype detection from circulating cell-free DNA in maternal plasma in non-sensitized RhD negative women", Prenat Diagn, 31:802-08 (2011).
Camaschella, et al., "Prenatal Diagnosis of Fetal Hemoglobin Lepore-Boston Disease on Maternal Peripheral Blood", Blood, 75(11):2102-06 (1990).
Cappuzzo, et al., "Epidermal growth factor receptor gene and protein and gefitinib sensitivity in non-small-cell lung cancer", J. Natl Cancer Inst., 97(9):643-55 (2005).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the *maspin* gene in maternal plasma", PNAS USA, 102(41):14753-58 (2005).
Chiu, et al, "Effects of Blood-Processing Protocols on Fetal and Total DNA Quantification in Maternal Plasma", Clin. Chem., 47(9):1607-1613 (2001).
Chiu, et al., "Maternal plasma DNA analysis with massively parallel sequencing by ligation for noninvasive prenatal diagnosis of trisomy 21", 56:459-63 (2010).
Chiu, et al, "Noninvasive prenatal diagnosis of fetal chromosomal aneuploidy by massively parallel genomic sequencing of DNA in maternal plasma", PNAS USA 105:20458-63 (2008).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al., "Non-invasive prenatal assessment of trisomy 21 by multiplexed maternal plasma DNA sequencing: large scale validity study", Br Med J. 342:c7401 (2011).
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Choo, et al., "A homologous subfamily of satellite III DNA on human chromosomes 14 and 22", Nucleic Acids Research, 18(19):5641-47 (1990).
Choo, et al., "A Chromosome 14-specific Human Satellite III DNA Subfamily That Shows Variable Presence on Different Chromosomes 14", Am J. Hum. Genet., 50:706-16 (1992).
Chromosome 14 map.
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cockwell, et al., "Distribution of the D15A1 copy number polymorphism", European J. of Hum. Genet., 15:441-45 (2007).
Conover, Practical Nonparametric Statistics, pp. 295-301 (John Wiley & Sons, NY)(1971).
Costa, et al., "New strategy for prenatal diagnosis of X-linked disorders", N. Engl J. Med., 346:1502 (2002).
Dear, et al., "A High-Resolution Metric HAPPY Map of Human Chromosome 14" Genmoics, 48 232-41 (1998).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Ehrich, et al., "Noninvasive detection of fetal trisomy 21 by sequencing of fetal DNA in maternal blood: a study in a clinical setting", AM J. Obstet Gynecol, 2011:204:205 e1-11 (2011).
Fan, et al., "Noninvasive diagnosis of fetal aneuploidy by shotgun sequencing DNA from maternal blood", PNAS USA, 105(42):16266-71 (2008).
Fan, et al., "Analysis of the Size Distributions of Fetal and Maternal Cell-Free DNA by Paired-End Sequencing", Clin. Chem., 56(8):1279-80 (2010).
Fan, et al., "Sensitivity of noninvasive prenatal detection of fetal aneuploidy from maternal plasma using shotgun sequencing is limited only by counting statistics", PLoS One, 5:e10439 (2010).

(56) References Cited

OTHER PUBLICATIONS

Fejgin, et al., "Fetal cells in the uterine cervix: a source for early non-invasive prenatal diagnosis", Prenat. Diag., 21:619-21 (2001).
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fowke, Genetic analysis of human DNA recovered from minute amounts of serum and plasma, J. of Immunol. Meth., 180:45-51 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Guatelli, et al., "Isothermal, in vitro amplification of nucleic acids by a multienzyme reaction modeled after retroviral replication", PNAS USA, 87(5):1874-(1990).
Han, et al, "Molecular Chytogenetic Characterization of 17 rob(13q14q) Robertsonian Translocations by FISH, Narrowing the Region Containing the Breakpoints", Am J. Hum. Genet., 55:960-67 (1994).
Harrell, Regression modeling strategies, §§9.2.2 and 1.10.5 (Springer Vertag)(2001).
Heilig, et al., "The DNA sequence and analysis of human chromosome 14", Nature, 421:601-09 (2003).
Hosny, et al., "TP53 mutations in circulating fee DNA from Egyptian patients with non-Hodgkin's lymphoma", Cancer Lett., 275(2):234-39 (2009).
Irizarry, et al., "Summaries of Affymetrix GeneChip probe level data", Nuc. Acid Res., 31(4):e5 (2003).
Kamnasaran and Cox, "Current status of chromosome 14", J. Med. Genet., 39:81-90 (2002).
Landegren, et al., "A ligase-mediated gene detection technique", Science, 241:1077 (1988).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, et al., "Detection of single-copy fetal DNA sequence from maternal blood", The Lancet, 335:1463-64 (1990).
Lo, et al., "Two-way cell traffic between mother and fetus: biological and clinical implications", Blood, 88:4390-95 (1996).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).
Lo, et al., "Prenatal diagnosis of fetal RhD status by molecular analysis of maternal plasma", N Engl J Med, 339:1734-38 (1998).
Lo, et al., "Rapid clearance of fetal DNA from maternal plasma", Am J. Hum. Genetics, 64:218-24 (1999).
Lo, et al., "Digital PCR for the molecular detection of fetal chromosomal aneuploidy", PNAS USA, 104:13116-21 (2007).
Lo, et al., "Plasma placental RNA allelic ratio permits noninvasive prenatal chromosomal aneuploidy detection", Nat. Med., 13:218-23 (2007).
Lo, et al., Maternal plasma DNA sequencing reveals the genome-wide genetic and mutational profile of the fetus. Sci Transl Med, 2:61ra91 (2010).
Lo, "Fetal nucleic acids in maternal blood: the promises", Clin. Chem. Lab Med., 50(5):xxx-xxx (DOI 10.1515/CCLM.2011.765) (2011).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Mujezinovic and Alfirevic, Obstet. Gynecol., "Procedure-Related Complications of Amniocentesis and Chorionic Villous Sampling: A Systematic Review", 110(3):687-94 (2007).
Mueller, et al., "Isolation of fetal trophoblast cells from peripheral blood of pregnant women", The Lancet, 336:197-200 (1990).
Nawroz, et al., "Microsatellite alterations in serum DNA of head and neck cancer patients", Nature Medicine, 2(9):1035-37 (1996).
Ng, et al., "mRNA of placental origin is readily detectable in maternal plasma", PNAS USA, 100:4748-53 (2003).
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
St. Clair, "Copy Number Variation and Schizophrenia", Schizophr. Bull., 35(1):9-12 (2009).
Savas, "Useful genetic variation databases for oncologists investigating the genetic basis of variable treatment response and survival in cancer", Acta Oncol., 49(8):1217-26 (2010).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Sebat, et al., "Strong Association of De Novo Copy Number Mutations with Autism", Science, 316(5823):445-49 (2007).

(56) References Cited

OTHER PUBLICATIONS

Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Simpson and Elias, "Isolating Fetal Cells from Maternal Blood", JAMA, 270(19):2357-61 (1993).
Simpson, "Is Cell-Free Fetal DNA from Maternal Blood Finally Ready for Prime Time?", Obst & Gynecol., 119(5):1-3 (2012).
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prey., 3_67-71 (1994).
Nicolaides, et al., "Validation of targeted sequencing of single-nucleotide polymorphisms for non-invasive prenatal detection of aneuploidy of chromosomes 13, 18, 21, X and Y", Prenatal Diagnosis, 33:1-5 (2013).
Palomaki, et al., "DNA sequencing of maternal plasma reliably identifies trisomy 18 and trisomy 13 as well as Down Syndrome: an international collaborative study", Genetics in Medicine, 14(3):296-305 (2012).
Jiang, et al., "Noninvasive Fetal Trisomy (NIFTY) test: an advanced noninvasive prenatal diagnosis methodology for fetal autosomal and sex chromosomal aneuploidies", BMC Medical Genomics, 5:57 (2012).
Tewhey, R. et al. (2009, e-published Nov. 1, 2009). "Microdroplet-based PCR enrichment for large-scale targeted sequencing," Nat Biotechnol 27(11):1025-1031; Supplementary materials: 26 pages.

\* cited by examiner

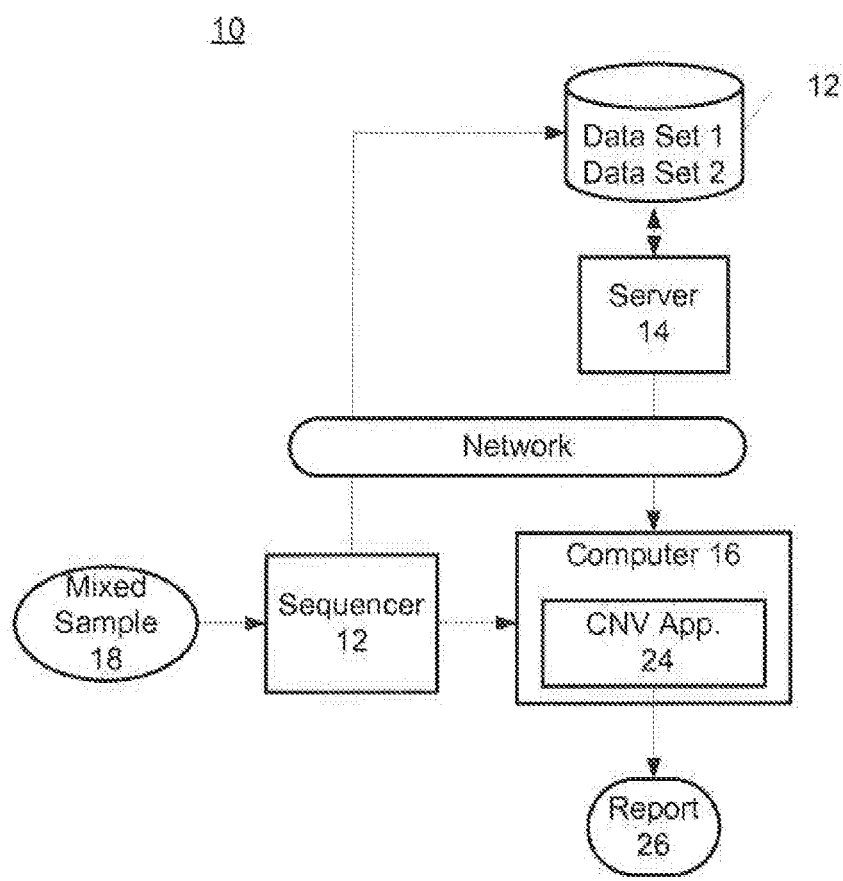

ASSAY SYSTEMS FOR DETERMINATION OF FETAL COPY NUMBER VARIATION

CROSS-REFERENCE TO RELATED APPLICATIONS

This application is a continuation-in-part of U.S. Ser. No. 13/338,963, now U.S. Pat. No. 8,700,338, filed Dec. 28, 2011, which is a continuation-in-part of U.S. Ser. No. 13/316,154, filed Dec. 9, 2011, which claims priority to U.S. Ser. No. 61/436,135, filed Jan. 25, 2011; this application also is a continuation-in-part of U.S. Ser. No. 13/205,570, now U.S. Pat. No. 9,890,421, filed Aug. 8, 2011, which is a continuation-in-part of U.S. Ser. No. 13/013,732, filed Jan. 25, 2011, which claims priority to U.S. Ser. No. 61/371,605, filed Aug. 6, 2010, all of which are incorporated by reference in their entireties.

FIELD OF THE INVENTION

The invention provides a non-invasive method for calculating the risk of fetal genomic copy number variations such as aneuploidies using maternal samples including maternal blood, plasma and serum.

BACKGROUND OF THE INVENTION

In the following discussion certain articles and processes will be described for background and introductory purposes. Nothing contained herein is to be construed as an "admission" of prior art. Applicant expressly reserves the right to demonstrate, where appropriate, that the articles and processes referenced herein do not constitute prior art under the applicable statutory provisions.

The American Congress of Obstetricians and Gynecologists (ACOG) recommends that pregnant women be offered non-invasive screening for fetal chromosomal abnormalities. As such existing screening methods exhibit false positive and negative rates in the range of 5% and 10% respectively, ACOG also recommends that patients categorized by screening as high risk for fetal aneuploidy be offered invasive testing such as amniocentesis or chorionic villus sampling. Although these invasive procedures are highly accurate, they are expensive and entail a risk of loss of normal fetus of approximately 0.5-1%. To address these limitations, non-invasive methods of fetal aneuploidy detection have been developed.

In particular, more recent attempts to identify aneuploidies have used maternal blood as a starting material. Such efforts have included the use of cell free DNA (cfDNA) to detect fetal aneuploidy in a sample from a pregnant female, including use of massively parallel shotgun sequencing (MPSS) to quantify precisely the increase in cfDNA fragments from trisomic chromosomes. The chromosomal contribution resulting from fetal aneuploidy, however, is directly related to the fraction of fetal cfDNA. Variation of fetal nucleic acid contribution between samples can thus complicate the analysis, as the level of fetal contribution to a maternal sample will vary the amounts needed to be detected for calculating the risk that a fetal chromosome is aneuploid.

For example, a cfDNA sample containing 4% DNA from a fetus with trisomy 21 should exhibit a 2% increase in the dosage of reads from chromosome 21 (chr21) as compared to a normal fetus. Distinguishing a trisomy 21 from a normal fetus with high confidence using a maternal sample with a fetal nucleic acid percentage of 4% requires a large number (>93K) of chromosome 21 observations, which is challenging and not cost-effective using non-selective techniques such as MPSS.

Thus, improved processes for the calculation of the risk of fetal genomic copy number variations, e.g., chromosomal contribution abnormalities such as aneuploidies, would be of great benefit in the art.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides methods for evaluating the risk of fetal genomic copy number variations, including but not limited to aneuploidies. Specifically, the invention provides processes for calculating risk probabilities to predict the presence or absence of a chromosomal abnormality such as a copy number variation or an aneuploidy.

In one general aspect, the invention provides a computer-implemented process for determining the presence or absence of a copy number variation in a fetal genomic region (e.g., locus or chromosome) comprising the steps of calculating an estimated dosage of a first fetal genomic region present in a maternal sample, calculating an estimated contribution of at least a second fetal genomic region in a maternal sample, and comparing the dosages of the first and second fetal genomic regions to determine the likelihood of a copy number variation in the first fetal genomic region.

In some aspects, the copy number variation determined using the methods of the invention is a chromosomal aneuploidy, and the dosages measure fetal chromosome dosage in a maternal sample. The presence or absence of a copy number variation of the first fetal genomic region can be estimated by interrogating at least twenty or more polymorphic loci in the first and second fetal genomic regions, and more preferably by interrogating at least fifty polymorphic loci in the first and second fetal genomic regions. The presence or absence of a copy number variation can also be estimated by interrogating at least five informative loci in the first and second fetal genomic regions, and more preferably by interrogating at least twenty informative loci in the first and fetal second genomic regions.

In a more specific aspect, the invention provides a computer-implemented process to calculate a risk of a fetal aneuploidy comprising estimating the dosage of a first fetal chromosome in a maternal sample, estimating the dosage of one or more other fetal chromosomes in the maternal sample, calculating a value of the likelihood that a first fetal chromosome is aneuploid by comparing the chromosome dosage of the first fetal chromosome to the chromosome dosage of the one or more other fetal chromosomes, calculating a value of the likelihood that the first fetal chromosome is disomic by comparing the chromosome dosage of the first fetal chromosome to the chromosome dosage of the one or more other fetal chromosomes in view of the prior risk of aneuploidy; and calculating a risk of aneuploidy of the first fetal chromosome based on the calculated values of likelihood.

In some aspects, the dosage of one fetal chromosome is compared to the dosage of one or more other individual fetal chromosomes. In other aspects the dosage of one fetal chromosome can be compared to an average dosage determined by interrogating two or more other fetal chromosomes and determining an average dosage.

In some aspects, the chromosome dosage of the first chromosome is estimated by interrogating at least twenty polymorphic loci on the first fetal chromosome, and more preferably by interrogating at least fifty polymorphic loci on the first fetal chromosome. In other aspects, the chromosome dosage of the first fetal chromosome is estimated by interrogating at least five informative loci on the first fetal chromosome, more preferably by at least 20 informative loci on the first fetal chromosome.

The chromosome dosage of the one or more other fetal chromosomes to which the chromosome dosage of the first fetal chromosome is compared can be estimated by interrogating at least five informative loci, or more preferably at least twenty informative loci, of which all may be on a single chromosome or which may be located on two or more chromosomes different from the first fetal chromosome.

In a specific aspect, the chromosome dosages are calculated for two fetal chromosomes in a maternal sample, and the risk of aneuploidy determined by a comparison of the chromosome dosages. In this aspect, at least twenty polymorphic loci are interrogated on each chromosome, and more preferably at least fifty polymorphic loci are interrogated on each chromosome. In other aspects, the chromosome dosage of the chromosomes is estimated by interrogating at least five informative loci on each chromosome, more preferably at least 20 informative loci.

In another general aspect, the invention provides a computer-implemented process to calculate a risk of a fetal aneuploidy comprising estimating the dosage of a first fetal chromosome in a maternal sample, estimating the dosage of one or more other fetal chromosomes in the maternal sample, providing data on prior risk of aneuploidy for at least the first fetal chromosome based on extrinsic characteristics, calculating a value of the likelihood that a first fetal chromosome is aneuploid by comparing the chromosome dosage of the first fetal chromosome to the chromosome dosage of the one or more other fetal chromosomes in view of the prior risk of aneuploidy, calculating a value of the likelihood that the first fetal chromosome is disomic by comparing the chromosome dosage of the first fetal chromosome to the chromosome dosage of the one or more other fetal chromosomes in view of the prior risk of aneuploidy, and calculating a risk of aneuploidy of the first fetal chromosome based on the calculated values of likelihood.

In some aspects, the invention utilizes a binomial probability distribution to determine the dosages of the different fetal chromosomes in a maternal sample. The binomial probability distribution utilizes frequency data from informative loci with distinguishing regions that allow identification and differentiation of nucleic acids from the different sources.

Preferably, the value of the probability of an aneuploidy is calculated as an odds ratio. In some aspects, when the odds ratio is to determine the likelihood of a monosomy, the value of the probability of an aneuploidy for the first fetal chromosome can be based on a value of the likelihood of the chromosome being monosomic and a value of the likelihood of the chromosome being disomic. In some aspects, the odds ratio is to determine the likelihood of a trisomy, and the value of the probability of a chromosome dosage abnormality for the first fetal chromosome is based on a value of the likelihood of the chromosome being trisomic and a value of the likelihood of the chromosome being disomic.

In some aspects of this embodiment, extrinsic factor(s) are used in the initial odds ratio calculation, including prior risk data or other information related to gestational age, maternal age, previous pregnancies, and the like. In certain aspects, the data on prior risk of aneuploidy comprises information related to maternal age. In other aspects, the data on prior risk of aneuploidy comprises information related to gestational age. In preferred aspects, the data on prior risk comprises information related to maternal age and gestational age.

Certain aspects of the invention further comprise adjusting an initially computed odds ratio using an extrinsic factor that may affect the odds ratio. Examples of such extrinsic factors include information related to maternal age, information related to gestational age, information related to previous pregnancies with aneuploid fetus, information on patient health, information on family history, and the like. Additional examples of extrinsic factors include laboratory results, such as PAPP-A, total hCG, beta-free hCG, alpha fetoprotein, unconjugated estriol and inhibin A, or ultrasound findings such as nuchal translucency. In preferred embodiments, the step of adjusting the computed odds ratio uses extrinsic factors related to both maternal age and gestational age.

In some preferred aspects of this embodiment, the maternal sample is a cell free maternal sample, and in preferred aspects the cell free maternal sample is maternal blood serum or plasma.

These determinations are a direct comparison of fetal chromosome dosages, and are not dependent on determining an overall dosage of fetal nucleic acids in a maternal sample relative to dosages of maternal chromosomes. It is thus a feature of the invention that only information on fetal nucleic acid dosage is utilized in the actual calculation of copy number variation or aneuploidy.

It is a distinguishing feature from other current methodologies that the copy number variation calculation itself does not require information on maternal nucleic acid dosage.

In a preferred aspect, the nucleic acid regions used for fetal chromosome dosage calculations of an individual subject are assayed in a single vessel. In a more preferred aspect, the nucleic acid regions undergo a universal amplification. In another preferred aspect, the nucleic acid regions are each counted an average of at least 200 times, more preferably at least 300 times, even more preferably 500 times.

It is another feature of the invention that individual fetal chromosome dosages used in the calculations of the invention may be determined in a variety of ways, including determination of polymorphic ratios of fetal chromosomes or the use of binomial probability distributions of the fetal chromosomes in a maternal sample.

DESCRIPTION OF THE FIGURES

FIG. 1 is a block diagram illustrating an exemplary system environment.

DETAILED DESCRIPTION OF THE INVENTION

The processes described herein may employ, unless otherwise indicated, conventional techniques and descriptions of molecular biology (including recombinant techniques), genomics, biochemistry, and sequencing technology, which are within the skill of those who practice in the art. Such conventional techniques include hybridization and ligation of oligonucleotides, next generation sequencing, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "*Oligonucleotide Synthesis: A Practical Approach*" IRL Press, London (1984); Nelson and Cox, *Lehninger, Principles of Biochemistry*, $3^{rd}$ Ed., W. H. Freeman Pub., New York (2000); and Berg et al., *Biochemistry*, $5^{th}$ Ed., W.H. Freeman Pub., New York (2002), all of which are herein incorporated by reference in their entirety for all purposes. Before the present compositions, research tools and processes are described, it is to be understood that this invention is not limited to the specific processes, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "an," and "the" include plural referents unless the context clearly dictates otherwise. Thus, for example, reference to "a nucleic acid region" refers to one, more than one, or mixtures of such regions, and reference to "an assay" includes reference to equivalent steps and processes known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein, and in particular patent applications and issued patents, are incorporated by reference for the purpose of describing and disclosing various aspects, details and uses of the processes and systems that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention.

DEFINITIONS

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication process performed in vitro as compared to the starting amount in a maternal sample.

The term "chromosome dosage" refers to the relative number of copies of chromosomes in a sample. In the present invention, fetal chromosome dosage for one or more specific chromosomes is determined by comparison to the chromosome dosage for one or more other fetal chromosomes in a maternal sample. That is, the fetal chromosome dosage calculation in the methods of the invention need not take into consideration maternal chromosome dosage. In one example, if the fetal chromosome dosages are 1.0, 1.0, 1.5, 1.0 and 0 for fetal chromosomes 1, 2, 21 and the X and Y chromosomes, respectively, it would appear that the fetus is a female, with a chromosome 21 trisomy. In another example, if the fetal chromosome dosages are 1.0, 1.0, 1.0, 0.5 and 0.5 for fetal chromosomes 1, 2, 21 and the X and Y chromosomes, respectively, it would appear that the fetus is a male, without a chromosome 21 trisomy. The term "chromosomal dosage abnormality" refers to duplications or deletions of all (aneuploidy) or part of a chromosome.

The term "diagnostic tool" as used herein refers to any composition or assay of the invention used in combination as, for example, in a system in order to carry out a diagnostic test or assay on a patient sample.

The term "DNA contribution" refers to the percentage, proportion or measurement such as weight by volume of nucleic acid in a sample that is contributed by a source, such as the mother or a fetus.

The term "extrinsic factor" includes any information pertinent to the calculation of an odds ratio that is not empirically derived through detection of a maternal and fetal locus. Examples of such extrinsic factors include information related to maternal age, information related to gestational age, information related to previous pregnancies with an aneuploid fetus, previous serum screening results, ultrasound findings and the like. In preferred embodiments, the step of calculating and/or adjusting the computed odds ratio uses extrinsic factors related to both maternal age and gestational age.

The term "genomic regions" refers to any genetic region comprising five or more informative loci.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The terms "locus" and "loci" as used herein refer to a nucleic acid region of known location in a genome.

The term "informative locus" as used herein refers to a locus with one or more distinguishing regions which is homozygous in one source and heterozygous in another source within a mixed sample.

The term "maternal sample" as used herein refers to any sample taken from a pregnant mammal which comprises a maternal source and a fetal source of nucleic acids (e.g., RNA or DNA).

The term "non-maternal" allele means an allele with a polymorphism and/or mutation that is found in a fetal allele (e.g., an allele with a de novo SNP or mutation) and/or a paternal allele, but which is not found in the maternal allele.

By "non-polymorphic", when used with respect to detection of selected nucleic acid regions, is meant a detection of such nucleic acid region which may contain one or more polymorphisms, but in which the detection is not reliant on detection of the specific polymorphism within the region. Thus, a selected nucleic acid region may contain a polymorphism, but detection of the region using the assay system of the invention is based on occurrence of the region rather than the presence or absence of a particular polymorphism in that region.

As used herein "polymerase chain reaction" or "PCR" refers to a technique for replicating a specific piece of target DNA in vitro, even in the presence of excess non-specific DNA. Primers are added to the target DNA, where the primers initiate the copying of the target DNA using nucleotides and, typically, Taq polymerase or the like. By cycling the temperature, the target DNA is repetitively denatured and copied. A single copy of the target DNA, even if mixed in with other, random DNA, can be amplified to obtain billions of replicates. The polymerase chain reaction can be used to detect and measure very small amounts of DNA and to create customized pieces of DNA. In some instances, linear amplification processes may be used as an alternative to PCR.

The term "polymorphism" as used herein refers to any genetic characteristic in a locus that may be indicative of that particular locus, including but not limited to single nucleotide polymorphisms (SNPs), methylation differences, short tandem repeats (STRs), and the like.

The term "polymorphic locus" as used herein refers to a locus with two or more detectable alleles within a population. Generally, a polymorphic locus will have the most common allele less than 70%.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a nucleic acid region to a capture oligonucleotide for detection of a specific nucleic acid region.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "selected nucleic acid region" as used herein refers to a nucleic acid region corresponding to a genomic region on an individual chromosome. Such selected nucleic acid regions may be directly isolated and enriched from the sample for detection, e.g., based on hybridization and/or other sequence-based techniques, or they may be amplified using the sample as a template prior to detection of the sequence. Nucleic acids regions for use in the processing systems of the present invention may be selected on the basis of DNA level variation between individuals, based upon specificity for a particular chromosome, based on CG content and/or required amplification conditions of the selected nucleic acid regions, or other characteristics that will be apparent to one skilled in the art upon reading the present disclosure.

The terms "sequencing", "sequence determination" and the like as used herein refers generally to any and all biochemical processes that may be used to determine the order of nucleotide bases in a nucleic acid.

The term "specifically binds", "specific binding" and the like as used herein, refers to one or more molecules (e.g., a nucleic acid probe or primer, antibody, etc.) that binds to another molecule, resulting in the generation of a statistically significant positive signal under designated assay conditions. Typically the interaction will subsequently result in a detectable signal that is at least twice the standard deviation of any signal generated as a result of undesired interactions (background).

The term "value of the likelihood" refers to any value achieved by directly calculating likelihood or any value that can be correlated to or otherwise indicative of a likelihood.

The term "value of the probability" refers to any value achieved by directly calculating probability or any value that can be correlated to or otherwise indicative of a probability.

The Invention in General

The present invention provides processes for determining the likelihood of a fetal copy number variation or an aneuploid chromosome in a fetus by directly comparing the level of fetal chromosome dosages from at least two fetal chromosomes without using maternal chromosome dosage as a direct comparator in the determination. Fetal DNA contribution to the maternal sample can be determined using various methods that distinguish the fetal nucleic acids from corresponding maternal nucleic acids. Once fetal DNA contribution in the maternal sample is determined, the dosage of specific fetal genomic regions (including chromosomes) can be compared to the dosages for other fetal chromosomes in the sample to identify any statistical differences that would indicate that one or more fetal genomic regions has a variation, e.g., a copy number variation or an aneuploidy. That is, the risk of fetal copy number variation or aneuploidy is determined by looking at only fetal chromosome dosage, without using maternal chromosome or locus dosage determinations.

Determination of Fetal DNA Contribution in a Maternal Sample

The fetal DNA contribution in a maternal sample is used as a part of the risk calculation of the present invention.

The fetal DNA contribution in the maternal sample used in the odds risk calculation can be estimated using a variety of techniques. The processes for detection include various strategies including but not limited to those described herein. One of skill in the art will recognize that any method by which one can estimate the contribution of a fetal DNA in a maternal sample can be used in determination of the fetal chromosome dosage, which in turn is used in the calculation of aneuploidy.

In general, the fetal DNA contribution can be determined relative to the overall DNA levels in a maternal sample, and the fetal DNA contribution can be used to identify genomic regions which are either overrepresented (as in the case on an extra copy of a genomic region) or underrepresented (as in the case of a missing copy of a genomic region).

In some aspects, fetal DNA contribution in the maternal sample can provide important information on the expected statistical presence of chromosomal dosage. Variation from the expected statistical presence may be indicative of fetal aneuploidy, and in particular a fetal trisomy or monosomy of a particular chromosome.

In certain aspects, determination of fetal polymorphisms requires targeted SNP and/or mutation analysis to identify the presence of fetal DNA in a maternal sample. In some aspects, prior genotyping of the father and/or mother may be used. For example, the parents may have undergone genetic screening to identify disease markers, e.g., markers for disorders such as cystic fibrosis, muscular dystrophy, spinal muscular atrophy or even the status of the RhD gene. Differences in polymorphisms, copy number variants or mutations between fetal and maternal nucleic acids can be used to determine the fetal DNA contribution in a maternal sample.

In one preferred aspect, the percent or proportion of fetal cell free DNA in a maternal sample can be quantified using multiplexed SNP detection without prior knowledge of the maternal or paternal genotype. In this aspect, two or more selected polymorphic nucleic acid regions with a known SNP in each region are used. In a preferred aspect, the selected polymorphic nucleic acid regions are located on an autosomal chromosome that is unlikely to be aneuploid, e.g., not chromosomes 21, 18, or 13. The selected polymorphic nucleic acid regions from the maternal sample (e.g., plasma) are amplified. In a preferred aspect, the amplification is universal; and in a preferred embodiment, the selected polymorphic nucleic acid regions are amplified in one reaction in one vessel. Each allele of the selected polymorphic nucleic acid regions in the maternal sample is determined and quantified. In a preferred aspect, high throughput sequencing is used for such determination and quantification.

Loci are thus identified where the maternal and fetal genotypes are different; e.g., the maternal genotype is homozygous and the fetal genotype is heterozygous. For example, identification of informative loci can be accomplished by observing a high frequency of one allele (>80%) and a low frequency (<20% and >0.15%) of the other allele for a particular selected nucleic acid region. The use of multiple loci is particularly advantageous as it reduces the amount of variation in the measurement of the abundance of the alleles between loci. All or a subset of the loci that meet this requirement within a genomic region of interest can be used to determine fetal DNA contribution in the maternal sample using statistical analysis, as described in more detail herein. In one aspect, fetal DNA contribution in the maternal sample is determined by summing the low frequency alleles from two or more loci together, dividing by the sum of the low and high frequency alleles and multiplying by two.

In one preferred embodiment, the present invention utilizes allelic information where there is a distinguishable difference between the fetal and maternal DNA (e.g., a fetal allele containing at least one allele that differs from the maternal allele) in determination of fetal DNA contribution in the maternal sample. Data pertaining to allelic regions that are the same for maternal and fetal DNA are thus not selected for analysis, or are removed from the pertinent data prior to determination of the fetal DNA contribution in the maternal sample so as not to mask the useful data. Additional exemplary processes for quantifying fetal DNA contribution in maternal plasma can be found, e.g., in Chu, et al., Prenat. Diagn., 30:1226-29 (2010), which is incorporated herein by reference.

In a related aspect, data from selected nucleic acid regions may be excluded from the calculation of fetal DNA contribution if the data from the region appears to be an outlier due to experimental error or from idiopathic genetic bias within a particular sample. In another aspect, selected data from certain nucleic acid regions may undergo statistical or mathematical adjustment such as normalization, standardization, clustering, or transformation prior to summation or averaging. In another aspect, data from selected nucleic acid regions may undergo both normalization and data experimental error exclusion prior to summation or averaging. The normalization may be performed for each of the dosages compared to determine the aneuploidy, or the normalization may be performed for one or a subset of the dosages compared to determine the aneuploidy.

Determination of Fetal DNA Contribution in a Maternal Sample Using Epigenetic Allelic Ratios.

Certain genes have been identified as having epigenetic differences between the fetus and the mother, and such genes are candidate loci for fetal DNA markers in a maternal sample. See, e.g., Chim SS, et al., PNAS USA, 102:14753-58 (2005). These loci, which are unmethylated in the fetus but are methylated in maternal blood cells, can be readily detected in maternal plasma. The epigenetic allelic ratio for one or more of such sequences known to be differentially-methylated in fetal DNA as compared to maternal DNA can be determined for a genomic region (e.g., a chromosome). The comparison of methylated and unmethylated amplification products from a maternal sample can then be used to quantify fetal DNA contribution in the maternal sample.

To determine methylation status of nucleic acids in a maternal sample, the nucleic acids of the sample are subjected to bisulfite conversion. Conventional processes for such bisulphite conversion include, but are not limited to, use of commercially available kits such as the Methylamp™ DNA Modification Kit (Epigentek, Brooklyn, N.Y.). Allelic frequencies and ratios can be directly calculated and exported from the data to determine the dosage of fetal genomic regions in the maternal sample.

Determination of Fetal Chromosome Dosage

When measuring chromosome or locus dosage, the fetal loci used to calculate chromosome dosage can be selected from a maternal sample prior to detection, i.e. selectively isolated from a maternal sample prior to detection using amplification or capture techniques such as hybridization. Alternatively, the fetal loci used in estimation of chromosome dosage may be selected after detection, e.g., by filtering frequency data generated from techniques such as massively parallel shotgun sequencing of nucleic acids within the maternal sample.

In some specific aspects, estimation of chromosome dosage employs highly-multiplexed sequencing of selected loci from specific chromosomes of interest. Chromosome-selective sequencing can be used to assay numerous loci simultaneously in a single reaction, enabling estimation of both fetal chromosome dosage of fetal DNA contribution in the maternal sample. Subsequently, a novel risk calculation of the invention can employed, which leverages chromosome dosage and fetal DNA contribution estimates to compute the likelihood of chromosomal dosage abnormalities (e.g., fetal trisomy) in each subject.

In a preferred example, the chromosome dosage for a fetal chromosome is determined on a chromosome-by-chromosome basis. For instance, frequency information for fetal chromosome 21 can be compared to fetal chromosome 18. In another example, the combined dosage of two or more chromosomes can be used as a comparator for determining an aneuploidy in a single chromosome, e.g., the chromosome dosages of chromosomes 1 and 2 can be used as a comparator for identifying the presence or absence of an aneuploidy in chromosome 21. In certain aspects, the chromosome used as a comparator for one chromosome may also be a chromosome interrogated for possible abnormalities, e.g., the chromosome dosage of chromosome 18 may be compared to the chromosome dosage of chromosome 21 to identify the presence or absence of an aneuploidy in either chromosome. In another aspect, the chromosome(s) used as a comparator specifically is not a chromosome interrogated for possible dosage abnormalities.

Determining which genetic loci are contributed to the fetus from non-maternal sources allows the estimation of fetal genomic region dosage (e.g., chromosome dosage) in a maternal sample, and thus provides information used to calculate statistically significant differences in the dosages for genomic regions (e.g., chromosomes) of interest.

In a general aspect, data from 20 or more polymorphic loci are used for analysis of fetal chromosome dosage. In another preferred aspect, data from 30 or more polymorphic loci are used for the analysis. In another preferred aspect, data from 40 or more polymorphic loci are used for the analysis. In another preferred aspect, data from 50 or more loci are used for the analysis. In another preferred aspect, data from 100 or more loci are used for the analysis. In another preferred aspect, data from 200 or more loci are used for the analysis.

In a preferred aspect, data from 5 or more informative loci are used for the analysis of fetal chromosome dosage. In another preferred aspect, data from 20 or more informative loci are used for the analysis. In another preferred aspect, data from 40 or more informative loci are used for the analysis. In another preferred aspect, data from 50 or more informative loci are used for the analysis. In another preferred aspect, data from 100 or more informative loci are used for the analysis. In another preferred aspect, data from 200 or more informative loci are used for the analysis.

In another aspect, one or more indices are used to identify the sample, the locus, the allele or the identification of the nucleic acid. Such indices are as described in co-pending applications 13/205,490 and 13/205,570 hereby incorporated herein by reference in their entirety.

In one preferred aspect, fetal chromosome dosage is quantified using tandem SNP detection in the maternal and fetal alleles. Techniques for identifying tandem SNPs in DNA extracted from a maternal sample are disclosed in Mitchell et al, U.S. Pat. No. 7,799,531 and U.S. patent application Ser. Nos. 12/581,070, 12/581,083, 12/689,924, and 12/850,588. These references describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample and used to determine the fetal frequency of genomic regions, including fetal chromosome dosage, in the maternal sample.

As described in relation to calculation of fetal DNA contribution previously, data from selected nucleic acid regions may be excluded from the calculation of fetal chromosome dosage if the data from the region appears to be an outlier due to experimental error or from idiopathic genetic bias within a particular sample. In another aspect, selected data from certain nucleic acid regions may undergo statistical or mathematical adjustment such as normalization, standardization, clustering, or transformation prior to summation or averaging. In another aspect, data from selected nucleic acid regions may undergo both normalization and data experimental error exclusion prior to summation or averaging. The normalization may be performed for each of the dosages compared to determine the aneuploidy, or the normalization may be performed for one or a subset of the dosages compared to determine the aneuploidy.

Empirical Techniques for the Estimation of Chromosome Dosage

Fetal chromosome dosage can be estimated using various different techniques, as will become apparent to one skilled in the art upon reading the present disclosure. Preferably, the techniques used involve determination of sequence differences between maternal and non-maternal sequences. This can be accomplished using array-based hybridization processes, such as those described in U.S. Pat. Pub. No. 2011/0172111. In other aspects, the biomolecules are detected using nanopore technology detection, such as those described in U.S. Pat. Pub. No. 2011/0124518. In preferred embodiments, the techniques used involve sequence determination of all or a portion of the fetal genomic regions used in the dosage calculations of the invention.

In certain aspects, the nucleic acids are sequenced and compared using polymorphisms that differentiate between maternal and fetal alleles in a sample, using methods such as those described in U.S. Pat. Nos. 7,727,720, 7,718,370, 7,598,060, 7,442,506, 7,332,277, 7,208,274, and 6,977,162. Briefly, the methods utilize polymorphic detection to identify chromosomal abnormalities. Sequences are determined at alleles that are homozygous in the mother and heterozygous in the fetus, and a ratio for the heterozygous alleles are determined. The ratio for the heterozygous alleles is used to indicate the presence or absence of a chromosomal abnormality.

In yet another aspect, estimation of chromosomal dosage abnormalities utilizes sequence identification of tandem polymorphisms, such as that described in, e.g., U.S. Pat. No. 7,799,531, and U.S. Pub. Nos. 2011/0117548, 2011/0059451, 2010/0184044, 2010/184043, and 2008/0020390. Briefly, tandem SNPs are detected and used to differentiate maternal and fetal alleles in a maternal sample to allow calculation of fetal chromosome dosages, thereby identifying fetal chromosomal abnormalities.

In a preferred aspect, the estimation of fetal chromosomal dosage utilizes selected amplification and sequence detection of representative loci. Such techniques are disclosed in, e.g., U.S. application Ser. Nos. 13/013,732, 13/205,490, 13/205,570, and 13/205,603, all of which are incorporated herein in their entirety. These techniques utilize detection of genomic regions using fixed sequence oligonucleotides and joining the fixed sequence oligonucleotides via ligation and/or extension. This can be accomplished using a combination of ligation and amplification, e.g., the ligation of two or more fixed sequence oligonucleotides and optionally a bridging oligonucleotide that is complementary to a region between the fixed sequence oligonucleotides. In another example, this can be accomplished using a combination of extension, ligation and amplification. In a preferred example the amplification is a universal amplification. Preferably, the amplification occurs in one vessel. Numerous methods of sequence determination are compatible with the assay systems of the inventions. Exemplary methods for sequence determination include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210, 891; Balasubramanian, U.S. Pat. Nos. 7,232,656 and 6,833, 246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Sequence information of fetal loci may be determined using methods that determine many (typically thousands to billions) of nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

Alternatively, in another aspect, the entire length of the amplification product or a portion of the amplification product may be analyzed using hybridization techniques. Methods for conducting polynucleotide hybridization assays for analyzing nucleic acids have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Patent application 60/364,731 and in PCT Application PCT/US99/06097 (published as WO99/47964), each of which also is hereby incorporated by reference in its entirety for all purposes.

Reference Sets for Calculating the Risk of Fetal Aneuploidy

In certain aspects of the invention, reference samples comprising one or more maternal samples with known levels of fetal chromosome dosages from patients carrying normal and/or abnormal (e.g., trisomic) fetuses can be used to identify risk of an aneuploidy. The fetal chromosome dosages present in one or more reference samples can be directly compared to fetal chromosome dosages in a test maternal sample to identify the risk of aneuploidy for a particular fetal chromosome. For example, chromosomal dosage estimations and variations can be calculated by comparing a test maternal sample to a reference maternal sample that has a corresponding level of fetal DNA contribution in the sample. As well as being matched based on overall fetal DNA contribution, reference maternal samples may be selected for comparison based on characteristics such as corresponding maternal age, corresponding gestational age, and the like.

These reference maternal samples can thus be used as a comparator for fetal chromosome dosage to identify the risk of an aneuploidy in a test maternal sample. Preferably, a test sample can be compared to one or more reference maternal samples from subjects carrying a diploid fetus and reference maternal samples from one or more subjects carrying a fetus that has an aneuploidy. The comparison of the test maternal sample to both reference samples can be used to calculate a value of the likelihood that the test maternal sample is from a subject carrying an aneuploidy fetus. The reference sample(s) may be tested in the same vessel or reaction as the maternal sample being tested. Differentiation of the test maternal sample results from the reference sample results could be accomplished by interrogating different loci in the reference sample(s) than the loci in the maternal sample being tested. Differentiation of the test maternal sample results also could be accomplished by interrogating the same loci in the reference sample(s) and test sample, but where there is a difference in sequence between the reference sample(s) versus the maternal sample being tested. The reference sample(s) may be synthesized or engineered to allow for these changes in sequence to be made. One likely advantage of having the reference sample(s) being in the same vessel or reaction as the maternal sample being tested is any assay variance would likely impact both the test and reference samples.

In one example, reference samples can be used as "normal" comparators for identifying the risk of a fetal aneuploidy. The fetal dosage of a genomic region (e.g., a chromosome of interest) in a test maternal sample can be compared to one or more appropriate corresponding normal reference samples that have approximately the same overall fetal DNA contribution in the reference sample as that found in the test sample. Test maternal samples with fetal chromosome or loci contribution(s) that fall outside normal range, as determined using the reference sample or samples, are identified as at risk of aneuploidy.

In another example, reference samples can be used as "affected" comparators for identifying the risk of a fetal aneuploidy. The dosage of one or more fetal genomic regions (e.g., a chromosome of interest) in a test maternal sample can be compared to one or more reference samples that have approximately the same overall fetal DNA contribution as the test sample and a known copy number variation, e.g., a trisomy. Test maternal samples that demonstrate a chromosome or locus contribution that falls within a range that corresponds to the known affected reference sample or samples, are identified as at risk of aneuploidy.

In some embodiments, chromosome dosages of a maternal test sample are compared to two or more reference samples that have a range of fetal DNA contribution relevant to the test maternal sample. In certain aspects, the range of fetal DNA contribution includes a range of two percentage points (e.g., 10-11%). In other aspects, the range of fetal DNA contribution includes a range of three percentage points (e.g., 8-10%). In yet other aspects, the range of fetal DNA contribution includes a range of four percentage points (e.g., 4-7%). In yet other aspects, the range of fetal DNA contribution includes a range of five percentage points (e.g., 5-9%).

In a more specific example, chromosome dosages of a specific fetal chromosome (e.g., chromosome 21) in a test maternal sample that has an empirically determined fetal DNA contribution of 5% can be compared to the fetal chromosome dosage of the same chromosome in a reference maternal sample that has also been determined to have an overall fetal DNA contribution of 5% and which is known to be from a subject carrying a diploid fetus. Alternatively, fetal chromosome dosages of a specific chromosome (e.g., chromosome 21) in a test maternal sample that has an empirically determined fetal DNA contribution of 5% can be compared to the chromosome dosage of two or more reference maternal samples that have been determined to have an overall fetal DNA contribution within an identified range, e.g., samples with fetal DNA contribution between 4-6% known to be from subjects carrying a diploid fetus. Test maternal samples with fetal chromosome dosages statistically greater than the determined range of normal defined by the reference samples would be identified as having an elevated risk of trisomy. Test maternal samples with chromosome dosages statistically lower than the determined range of normal defined by the reference samples would be identified as having an elevated risk of monosomy.

In another example, chromosome dosages of a specific fetal chromosome (e.g., chromosome 21) in a test maternal sample that has an empirically determined fetal DNA contribution of 7% can be compared to the chromosome dosage of that chromosome in a reference maternal sample that has also been determined to have an overall fetal DNA contribution of 7% and which is known to be from a subject carrying a fetus with an aneuploidy (e.g., trisomy 21). Alternatively, fetal chromosome dosages of a specific chromosome (e.g., chromosome 21) in a test maternal sample that has an empirically determined fetal DNA contribution of 7% can be compared to the chromosome dosage of two or more reference maternal samples that have been determined to have an overall fetal DNA contribution within an identified range, e.g., samples with fetal DNA contribution between 5-9% known to be from subjects carrying a fetus with an aneuploidy (e.g., trisomy 21). Test maternal samples with fetal chromosome dosages statistically greater than the determined range of normal defined by the reference samples would be identified as having an elevated risk of trisomy. Test maternal samples with fetal chromosome dosages statistically lower than the determined range of normal defined by the reference samples would be identified as having an elevated risk of monosomy.

Multiple reference samples can form a reference set that can be used as comparators for multiple test maternal samples with varying, specific characteristics, and thus would be useful as comparators for wider populations of patients. Such a reference sample set would preferably include reference samples that represent different ranges of fetal DNA contribution, as well as different dosage frequencies for one or more chromosomes or loci of interest. Such reference sample sets may be created using 2 or more, or preferably 5 or more samples from subjects with a diploid fetus, where the different samples in the reference set have different levels of fetal DNA contribution. In addition, reference sets may be further refined by sample characteristics such as corresponding maternal age, corresponding gestational age, and the like.

In a preferred aspect, the loci selected for analysis in the maternal test sample include in a single reaction both loci for determination of fetal DNA contribution as well as loci of interest corresponding to one or more chromosome(s) or one or more portion(s) of a chromosome of interest for determination of dosage. Use of a single reaction helps to minimize the risk of contamination or bias that may be introduced using separate reactions, which may otherwise skew results. In fact, the methods of the present invention are preferably performed as multiplexed or even highly-multiplexed reactions, where loci for determining fetal DNA contribution and chromosome dosage are interrogated in a single reaction for each sample. In preferred embodiments, the multiplexing assays described in U.S. application Ser. Nos. 13/013,732, 13/205,490, 13/205,570, and 13/205,603 are used, as these assays query both polymorphic and non-polymorphic loci in a maternal sample in a single multiplexed reaction.

In addition to the methods described earlier, the variation in the assay may be reduced when all of the nucleic acid regions for each sample are interrogated in a single reaction in a single vessel. Similarly, the variation in the assay may be reduced when a universal amplification system is used. Furthermore, the variation of the assay may be reduced when the number of cycles of amplification is limited.

Universal Amplification

In preferred aspects of the invention, the nucleic acid loci are preferably amplified in a multiplexed assay system. This is preferably done through use of universal amplification of the various loci to be analyzed using the assay systems of the invention. Universal primer sequences are added to the amplification products either during or following selective amplification of loci of interest, so that the loci may be further amplified in a single universal amplification reaction. For example, universal primer sequences may be added to the during the selective amplification process, i.e., the primers for selective amplification have universal primer sequences that flank a locus. Alternatively, adapters comprising universal amplification sequences can be added to the ends of the loci selected for amplification as adapters following amplification and isolation of the selected nucleic acids from the mixed sample.

In one exemplary aspect, nucleic acids are initially amplified from a maternal sample using primers comprising a region complementary to selected regions or loci of the chromosomes of interest and universal priming sites. The initial selective amplification is followed by a universal amplification step to increase the number of nucleic acid regions for analysis. This introduction of primer regions to the initial amplification products allows a subsequent controlled universal amplification of all or a portion of selected nucleic acids prior to or during analysis, e.g., sequence determination.

Bias and variability can be introduced during DNA amplification, such as that seen during polymerase chain reaction (PCR). In cases where an amplification reaction is multiplexed, there is the potential that loci will amplify at different rates or efficiency. Part of this may be due to the variety of primers in a multiplex reaction with some having better efficiency (i.e. hybridization) than others, or some working better in specific experimental conditions due to the base composition. Each set of primers for a given locus may behave differently based on sequence context of the primer and template DNA, buffer conditions, and other conditions. A universal DNA amplification for a multiplexed assay system will generally introduce less bias and variability.

Accordingly, in a preferred aspect, a small number (e.g., 1-10, preferably 3-5) of cycles of selective amplification or nucleic acid enrichment in a multiplexed mixture reaction are performed, followed by universal amplification using introduced universal priming sites. The number of cycles using universal primers will vary, but will preferably be at least 10 cycles, more preferably at least 15 cycles, even more preferably 20 cycles or more. By moving to universal amplification following one or a few selective amplification cycles, the bias of having certain loci amplify at greater rates than others is reduced.

Optionally, the assay system will include a step between the selective amplification and universal amplification to remove any excess nucleic acids that are not specifically amplified in the selective amplification.

The whole product or an aliquot of the product from the selective amplification may be used for the universal amplification. The same or different conditions (e.g., polymerase, buffers, and the like) may be used in the amplification steps, e.g., to ensure that bias and variability is not inadvertently introduced due to experimental conditions. In addition, variations in primer concentrations may be used to effectively limit the number of sequence specific amplification cycles.

In certain aspects, the universal primer regions of the primers or adapters used in the assay system are designed to be compatible with conventional multiplexed assay methods that utilize general priming mechanisms to analyze large numbers of nucleic acids simultaneously in one reaction in one vessel. Such "universal" priming methods allow for efficient, high volume analysis of the quantity of nucleic acid regions present in a mixed sample, and allow for comprehensive quantification of the presence of nucleic acid regions within such a mixed sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420, which is incorporated herein by reference.

Some aspects utilize coupled reactions for multiplex detection of nucleic acid sequences where oligonucleotides from an early phase of each process contain sequences which may be used in processes used in one or more later phases of the method. Exemplary processes for amplifying and/or detecting nucleic acids in samples can be used, alone or in combination, including but not limited to the methods described below, each of which are incorporated by reference in their entirety for purposes of teaching various elements that can be used in the assay systems of the invention.

In certain aspects, the assay system of the invention utilizes one of the following combined selective and universal amplification techniques: (1) LDR coupled to PCR; (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used in processes used in a later phase of the method.

Barany et al., U.S. Pat. Nos. 6,852,487, 6,797,470, 6,576, 453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429, 453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe the use of the ligase detection reaction ("LDR") coupled with polymerase chain reaction ("PCR") for nucleic acid detection.

Barany et al., U.S. Pat. Nos. 7,556,924 and 6,858,412, describe the use of padlock probes (also called "precircle probes" or "multi-inversion probes") with coupled ligase detection reaction ("LDR") and polymerase chain reaction ("PCR") for nucleic acid detection.

Barany et al., U.S. Pat. Nos. 7,807,431, 7,709,201, and 7,198,814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping.

Ronaghi et al., U.S. Pat. No. 7,622,281 describes amplification techniques for labeling and amplifying a nucleic acid using an adapter comprising a unique primer and a barcode.

In addition to the various amplification techniques, numerous methods of sequence determination are compatible with the assay systems of the inventions. Preferably, such methods include "next generation" methods of sequencing. Exemplary methods for sequence determination include, but are not limited to, hybridization-based methods, such as disclosed in Drmanac, U.S. Pat. Nos. 6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Alternatively, nucleic acid regions of interest can be selected and/or identified using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194

(1983). Methods and apparatus for carrying out repeated and controlled hybridization reactions have been described in U.S. Pat. Nos. 5,871,928, 5,874,219, 6,045,996 and 6,386,749, 6,391,623.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964).

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964).

Computer Implementation of the Processes of the Invention

FIG. 1 is a block diagram illustrating an exemplary system environment in which the processes of the present invention may be implemented for calculating chromosome or loci dosage and fetal DNA contribution. The system 10 includes a server 14 and a computer 16. The computer 16 may be in communication with the server 14 through the same or different network.

According to the exemplary embodiment, the computer 16 executes a software component 24 that calculates fetal chromosome dosage and/or fetal DNA contribution. In one embodiment, the computer 16 may comprise a personal computer, but the computer 16 may comprise any type of machine that includes at least one processor and memory.

The output of the software component 24 comprises a report 26 with a value of probability that a locus or genomic region and/or a chromosome has a dosage abnormality. In a preferred aspect this report is an odds ratio of a value of the likelihood that a region or chromosome has two copies (e.g., is disomic) and a value of the likelihood that a region or chromosome has more copies (e.g., is trisomic) or less copies (e.g., is monosomic) copies. The report 26 may be paper that is printed out, or electronic, which may be displayed on a monitor and/or communicated electronically to users via e-mail, FTP, text messaging, posted on a server, and the like.

Although the process of the invention is shown as being implemented as software 24, it can also be implemented as a combination of hardware and software. In addition, the software 24 may be implemented as multiple components operating on the same or different computers.

Both the server 14 and the computer 16 may include hardware components of typical computing devices (not shown), including a processor, input devices (e.g., keyboard, pointing device, microphone for voice commands, buttons, touchscreen, etc.), and output devices (e.g., a display device, speakers, and the like). The server 14 and computer 16 may include computer-readable media, e.g., memory and storage devices (e.g., flash memory, hard drive, optical disk drive, magnetic disk drive, and the like) containing computer instructions that implement the functionality disclosed when executed by the processor. The server 14 and the computer 16 may further include wired or wireless network communication interfaces for communication.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1

Subjects

Subjects are enrolled upon providing informed consent under protocols approved by institutional review boards. Subjects are required to be at least 18 years of age, at least 10 weeks gestational age, and to have singleton pregnancies. A subset of enrolled subjects, consisting of 250 women with disomic pregnancies, 72 women with trisomy 21 (T21) pregnancies, and 16 women with trisomy 18 (T18) pregnancies, are selected for inclusion in the study. The subjects are randomized into a cohort consisting of 130 disomic pregnancies, 30 T21 pregnancies, and 9 T18 pregnancies. The trisomy status of each pregnancy is confirmed by invasive testing (fluorescent in-situ hybridization and/or karyotype analysis) following the analysis provided using the assay of the invention, as described below.

Example 2

Assessment of Fetal Chromosome Dosage of Two Individual Fetal Chromosomes in a Maternal Sample To assess fetal nucleic acid dosage of genomic regions of interest in the maternal samples, assays are designed against a set of 150 SNP-containing loci on each of chromosomes 21 and 18. Each assay consists of three locus specific oligonucleotides: a left oligo with a 5' universal amplification tail, a 5' phosphorylated middle oligo, and a 5' phosphorylated right oligo with a 3' universal amplification tail. Two middle oligos differing by one base are used to query each SNP in the selected loci. SNPs are optimized for minor allele frequency in the HapMap 3 dataset. Duan, et al., Bioinformation, 3(3):139-41 (2008); Epub 2008 Nov. 9.

Oligonucleotides are synthesized by IDT (Coralville, Iowa) and pooled together to create a single multiplexed assay pool. PCR products are generated from each subject sample as described in U.S. Ser. No. 13/013,732, filed Jan. 25, 2011; and U.S. Ser. No. 13/205,570, filed Aug. 8, 2011, which are incorporated herein by reference in their entirety. Briefly, 8 ml blood per subject is collected into a glass tube comprising preservatives (Streck, Omaha, Nebr.) and stored at room temperature for up to 3 days. Plasma is isolated from blood via double centrifugation and stored at −20° C. for up to a year. cfDNA is isolated from plasma using Viral NA DNA purification beads (Life Technologies, Carlsbad, Calif.), biotinylated, immobilized on MyOne C1 streptavidin beads (Life Technologies, Carlsbad, Calif.), and annealed with the multiplexed oligonucleotide pool. Appropriately hybridized oligonucleotides are catenated with Taq ligase, eluted from the cfDNA, and amplified using universal PCR primers. PCR products from 96 independent samples are pooled and used as template for cluster amplification on a single lane of a TruSeq™ V3 SR flow slide (Illumina, San Diego, Calif.). The slide is processed on an Illumina HiSeg™ 2000 to produce a 56 base locus-specific sequence and a 7 base sample tag sequence from an average of 1.18M clusters/sample.

Because the assay exhibits allele specificities exceeding 99%, informative loci are readily identified when the fetal allele dosage of a locus is measured to be between 1 and 20%. A maximum likelihood is estimated using a binomial distribution, such as that described in co-pending application 61/509,188, filed Jul. 19, 2011, to determine the most likely fetal dosage of each of chromosome 18 and 21 based upon measurements from five or more informative loci. Since the likelihood that both chromosome 18 and 21 will exhibit a trisomy is extremely low (outside a triploid fetus), the initial risk of aneuploidy for chromosome 21 and chromosome 18 can be calculated using a computer model that compares the relative dosage of fetal chromosome 18 in a sample to the relative dosage of fetal chromosome 21 in the same maternal sample.

Example 3

Aneuploidy Detection Using Comparison of Dosages of Fetal Chromosome 18 and Fetal Chromosome 21

The initial risk of trisomy for chromosome 18 or 21 is further optimized using an odds ratio that compares a model assuming a disomic fetal chromosome and a model assuming a trisomic fetal chromosome. The distribution of differences in observed and reference dosages are evaluated using normal distributions with a mean of 0 and standard deviation estimated using Monte Carlo simulations that randomly draw from observed data. For the disomic model, p0 is used as the expected reference dosage in the simulations. For the trisomic model, p0 is adjusted on a per sample basis with the fetal dosage adjusted reference dosage $\hat{p}_j$, defined as $$\hat{p}_j = \frac{(1 + 0.5 f_j) p_0}{((1 + 0.5 f_j) p_0) + (1 - p_0)}$$

where $f_j$ was the fetal dosage for sample j. This adjustment accounts for the expected increased representation of a test chromosome when the fetus is trisomic. In the simulations both p0 and $f_j$ are randomly chosen from normal distributions using their mean and standard error estimates to account for measurement variances. Simulations are executed 100,000 times. The risk score is defined as the mean trisomy versus disomy odds ratio obtained from the simulations, adjusted by multiplying the risk of trisomy associated with the subject's maternal and gestational age.

The risk calculation algorithm used in calculation of the estimated risk of aneuploidy uses an odds ratio comparing a mathematic model assuming a disomic fetal chromosome and a mathematic model assuming a trisomic fetal chromosome. When $x_j = p_j - p_0$ is used to describe the difference of the observed dosage $p_j$ for sample j and the estimated reference dosage $p_0$, the risk calculation algorithm used computed:

$$\frac{P(x_j | T)}{P(x_j | D)},$$

where T was the trisomic model and D was the disomic model. The disomic model D was a normal distribution with mean 0 and a sample specific standard deviation estimated by Monte Carlo simulations as described below. The trisomic model T was also a normal distribution with mean 0, determined by transforming $x_j$ to $\hat{x}_j = p_j - \hat{p}_j$, the difference between the observed dosage and a fetal fraction adjusted reference dosage as defined by:

$$\hat{p}_j = \frac{(1 + 0.5 f_j) p_0}{((1 + 0.5 f_j) p_0) + (1 - p_0)}$$

where $f_j$ was the fetal fraction for sample j. This adjustment accounted for the expected increased representation of a trisomic fetal chromosome. Monte Carlo simulations were used to estimate sample specific standard deviations for disomic and trisomic models of dosage differences. Observed dosages for each sample were simulated by non-parametric bootstrap sampling of loci and calculating means, or parametric sampling from a normal distribution using the mean and standard error estimates for each chromosome from the observed non-polymorphic locus counts. Similarly, the reference dosage p0 and fetal fraction $f_j$ were simulated by non-parametric sampling of samples and polymorphic loci respectively, or chosen from normal distributions using their mean and standard error estimates to account for measurement variances. Parametric sampling was used in this study. Simulations were executed 100,000 times, and dosage differences were computed for each execution to construct the distributions. Based on the results of these simulations, normal distributions were found to be good models of disomy and trisomy.

The final risk calculation algorithm risk score is defined as $$\frac{P(x_j | T) P(T)}{P(x_j | D) P(D)}$$

where P(T)/P(D) is the prior risk of trisomy vs. disomy. The data on prior risk of aneuploidy was taken from well-established tables capturing the risk of trisomy associated with the subject's maternal and gestational age (Nicolaides KH. Screening for chromosomal defects. Ultrasound Obstet Gynecol 2003; 21:313-321).

Example 4

Assessment of Fetal Chromosome Dosage of One Individual Fetal Chromosome and Two or More Comparative Chromosomes in a Maternal Sample Assays are designed against a set of 20 SNP-containing loci on chromosome X outside the pseudoautosomal region, 20 SNP-containing loci on chromosome X within the pseudoautosomal region, and 20 SNP-containing loci distributed amongst chromosomes 1-10. Each assay consists of three locus specific oligonucleotides: a left oligo with a 5' universal amplification tail, a 5' phosphorylated middle oligo, and a 5' phosphorylated right oligo with a 3' universal amplification tail. Two middle oligos differing by one base are used to query each SNP in the selected loci. SNPs are optimized for minor allele frequency in the HapMap 3 dataset. Duan, et al., Bioinformation, 3(3):139-41 (2008); Epub 2008 Nov. 9.

Oligonucleotides are synthesized by IDT (Coralville, Iowa) and pooled together to create a single multiplexed assay pool. PCR products are generated from each subject sample as described in U.S. Ser. No. 13/013,732, filed Jan. 25, 2011; and U.S. Ser. No. 13/205,570, filed Aug. 8, 2011. Briefly, 8 ml blood per subject is collected into a glass tube comprising preservatives (Streck, Omaha, Nebr.) and stored at room temperature for up to 3 days. Plasma is isolated from blood via double centrifugation and stored at −20° C. for up to a year. cfDNA is isolated from plasma using Viral NA DNA purification beads (Life Technologies, Carlsbad, Calif.), biotinylated, immobilized on MyOne C1 streptavidin beads (Life Technologies, Carlsbad, Calif.), and annealed with the multiplexed oligonucleotide pool. Appropriately hybridized oligonucleotides are catenated with Taq ligase, eluted from the cfDNA, and amplified using universal PCR primers. PCR products from 96 independent samples are pooled and used as template for cluster amplification on a single lane of a TruSeq™ V3 SR flow slide (Illumina, San Diego, Calif.). The slide is processed on an Illumina HiSeg™ 2000 to produce a 56 base locus-specific sequence and a 7 base sample tag sequence from an average of 1.18M clusters/sample.

A maximum likelihood is estimated using a binomial distribution, such as that described in co-pending application 61/509,188, filed Aug. 8, 2011 to determine the most likely fetal dosage of chromosome X and collective fetal dosage of non-aneuploid chromosomes 1-10 based upon measurements from five or more informative loci. Since chromosomes 1-10 are not expected to exhibit any evidence of aneuploidy, the fetal concentration calculated across these chromosomes can be used as a direct comparator with the calculated contribution of chromosome X for determining the risk of either monosomy or trisomy of chromosome X.

The presence of trisomy X can be determined by a direct comparison of the contribution of the fetal X as determined inside and/or outside the pseudoautosomal regions compared to the fetal contribution calculated from the collective data of fetal chromosome 1-10.

The presence of monosomy X requires distinguishing an XO monosomy genotype from the presence of an XY normal genotype. The initial determination of monosomy can be calculated by a comparison of the contribution of the fetal X as determined outside the pseudoautosomal region. The genotype is then further distinguished by comparison to the fetal X contribution inside the pseudoautosomal regions which are in common with the Y chromosome, or by combining the assay with detection of a Y sequence in the maternal sample. The disomic levels of fetal X as determined inside the pseudoautosomal region or other detection of the presence of Y combined with a determination of the fetal X monosomy is indicative of a male genotype rather than XO.

While this invention is satisfied by aspects in many different forms, as described in detail in connection with preferred aspects of the invention, it is understood that the present disclosure is to be considered as exemplary of the principles of the invention and is not intended to limit the invention to the specific aspects illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

We claim:

1. A method for determining a likelihood of the presence or absence of a copy number variation (CNV) in a fetal genomic region in a maternal sample from a pregnant female, comprising:
    a) obtaining the maternal sample from the pregnant female, the maternal sample comprising a fetal source and a maternal source;
    b) executing, by a CNV processing system, a process for determining the likelihood of the presence or absence of CNV in the fetal genomic region, the process comprising the following steps:
        1) interrogating at least twenty polymorphic loci in a first fetal genomic region in the maternal sample and interrogating at least twenty polymorphic loci in a second fetal genomic region of the maternal sample;
        2) determining fetal DNA contribution to the maternal sample;
        3) calculating an estimated dosage of the first fetal genomic region in the maternal sample and calculating an estimated dosage of at least the second fetal genomic region in the maternal sample; and
        4) comparing the estimated dosages of the first and second fetal genomic regions to determine the likelihood of the presence or absence of the CNV in the first fetal genomic region in view of the fetal DNA contribution to the maternal sample; and
    c) assisting in a communication of the determined likelihood of the presence or absence of the CNV in the first fetal genomic region to the pregnant female.

2. The process of claim 1, wherein the maternal sample is a cell free maternal sample.

3. The process of claim 2, wherein the cell free maternal sample is maternal plasma or serum.

4. The process of claim 1, wherein the copy number variation is a chromosomal aneuploidy, and wherein the calculated contributions measure fetal chromosome dosage.

5. The process of claim 1, wherein the presence or absence of a copy number variation of the first genomic region is estimated by interrogating at least fifty polymorphic loci in the first and second genomic regions.

6. The process of claim 1, wherein the presence or absence of a copy number variation is estimated by interrogating at least five informative loci in the first and second genomic regions.

7. The process of claim 1, wherein the presence or absence of a copy number variation is estimated by interrogating at least twenty informative loci in the first and second genomic regions.

8. A method to calculate a risk of a fetal aneuploidy in a maternal serum or plasma sample from a pregnant female comprising:
    a) obtaining the maternal sample from the pregnant female, the maternal sample comprising a fetal source and a maternal source;
    b) executing, by a fetal aneuploidy processing system, a process comprising the following steps:
        i. interrogating at least twenty polymorphic loci on a first fetal chromosome in the maternal sample and interrogating at least twenty polymorphic on a second fetal chromosome in the maternal sample;
        ii. identifying genetic loci contributed to a fetus from non-maternal sources;

iii. determining fetal DNA contribution to the maternal sample;
iv. determining a relative number of copies of the first fetal chromosome in the maternal sample;
v. estimating the chromosome dosage of the first fetal chromosome in the maternal sample using the determined relative number of copies;
vi. determining a relative number of copies of the second fetal chromosome in the maternal sample;
vii. estimating the chromosome dosage of the second fetal chromosome in the maternal sample using the determined relative number of copies;
viii. calculating a value of the likelihood that a first fetal chromosome is aneuploid by constructing an aneuploid model by comparing the estimated chromosome dosage of the first fetal chromosome to the estimated chromosome dosage of the second fetal chromosome in view of the fetal DNA contribution to the maternal sample;
ix. calculating a value of the likelihood that the first fetal chromosome is disomic by constructing a disomic model by comparing the estimated chromosome dosage of the first fetal chromosome to the estimated chromosome dosage of the second fetal chromosome; and
x. providing a calculated risk of aneuploidy of the first fetal chromosome based on the calculated values of likelihood that the first fetal chromosome is aneuploid and the first fetal chromosome is disomic using an odds ratio comparing the model assuming a disomic first fetal chromosome and the model assuming an aneuploid first fetal chromosome adjusted by a prior risk of trisomy and disomy; and
c) assisting in a communication of the calculated risk of aneuploidy of the first fetal chromosome to the pregnant female.

9. The process of claim 8, wherein the maternal sample comprises cells.

10. The process of claim 8, wherein the chromosome dosage of the first chromosome is estimated by interrogating at least fifty polymorphic loci on the first chromosome.

11. The process of claim 8, wherein the chromosome dosage of the first chromosome is estimated by interrogating at least five informative loci on the first chromosome.

12. The process of claim 11, wherein the chromosome dosage of the first chromosome is estimated by interrogating at least twenty informative loci on the first chromosome.

13. The process of claim 8, wherein the value of the probability of an aneuploidy is an odds ratio.

14. The process of claim 8, wherein the risk of aneuploidy of the first fetal chromosome is based on a value of the likelihood of the first fetal chromosome being trisomic and the value of the likelihood of the first fetal chromosome being disomic.

15. The process of claim 8, wherein the value of the probability of a chromosome dosage abnormality for the first fetal chromosome is based on a value of the likelihood of the chromosome being monosomic and a value of the likelihood of the chromosome being disomic.

16. The process of claim 8, wherein the determining the fetal DNA contribution to the maternal sample step is accomplished by quantifying SNPs using multiplexed SNP detection without prior knowledge of maternal or paternal genotype.

17. The process of claim 8, wherein the determining the fetal DNA contribution to the maternal sample step is accomplished by quantifying SNPs where maternal and fetal genotypes are different.

18. The process of claim 8, wherein the determining the fetal DNA contribution to the maternal sample step is accomplished by epigenetic differences between the fetus and mother.

* * * * *